United States Patent [19]

Hauser et al.

[11] Patent Number: 5,052,407
[45] Date of Patent: Oct. 1, 1991

[54] CARDIAC DEFIBRILLATION/CARDIOVERSION SPIRAL PATCH ELECTRODE

[75] Inventors: Robert G. Hauser, Long Lake; Ronald W. Heil, Roseville; Robert C. Owens, Forest Lake, all of Minn.

[73] Assignee: Mieczyslaw Mirowski, Owings Mills, Md.

[21] Appl. No.: 334,652

[22] Filed: Apr. 10, 1989

Related U.S. Application Data

[63] Continuation-in-part of Ser. No. 181,432, Apr. 14, 1988, abandoned.

[51] Int. Cl.$^5$ .............................................. A61N 1/00
[52] U.S. Cl. ............................ 128/786; 128/419 P; 128/419 D
[58] Field of Search ............... 128/419 P, 419 D, 786

[56] References Cited

U.S. PATENT DOCUMENTS

| 3,348,548 | 10/1967 | Chardack | 128/418 |
|---|---|---|---|
| 3,516,412 | 6/1970 | Ackerman | 128/418 |
| 3,568,660 | 3/1971 | Crites et al. | 128/2 |
| 3,572,344 | 3/1971 | Bolduc | 128/418 |
| 3,729,008 | 4/1973 | Berkovits | 128/418 |
| 3,865,118 | 2/1975 | Bures | 128/419 P |
| 3,866,615 | 2/1975 | Hewson | 128/419 |
| 4,289,138 | 9/1981 | Halvorsen | 128/419 P |
| 4,357,947 | 11/1982 | Littleford | 128/786 |
| 4,374,527 | 2/1983 | Iversen | 128/785 |
| 4,394,866 | 7/1983 | Hughes | 128/785 |
| 4,401,126 | 8/1983 | Reenstierna | 178/784 |
| 4,401,127 | 8/1983 | Littleford | 128/786 |
| 4,402,330 | 9/1983 | Lindemans | 128/786 |
| 4,454,888 | 6/1984 | Gold | 128/785 |
| 4,481,953 | 11/1984 | Gold et al. | 128/786 |
| 4,552,157 | 11/1985 | Littleford | 128/786 |
| 4,567,900 | 2/1986 | Moore | 128/419 D |
| 4,567,901 | 2/1986 | Harris | 128/786 |
| 4,721,118 | 1/1988 | Harris | 128/419 P |
| 4,860,769 | 8/1989 | Fogarty et al. | 128/786 |
| 4,865,037 | 9/1989 | Chin et al. | 128/786 |

FOREIGN PATENT DOCUMENTS

| 0095726 | 7/1983 | European Pat. Off. | 128/419 D |
|---|---|---|---|
| 0095727 | 12/1983 | European Pat. Off. | |
| 87/04355 | 7/1987 | World Int. Prop. O. | 128/419 P |

OTHER PUBLICATIONS

Abstracts Circulation, vol. 76, Supp IV, Oct. 1987, p. IV-462, A New Internal Defibrillation Lead System.
Medical Instrumentation, vol. 15, No. 5, Oct. 81, pp. 329-330, If Successful Defibrillation is the Question, The R2 Apex-Posterior Electrode is the Answer.
Mansfield Scientific, Inc., TVF102, Ventri-Stat Flare Temporary Emergency Transthoracic Pacing Electrode Kit.
"New Stable Temporary Atrial Pacing Loop", Stephen C. Berens M.D., et al., *The American Journal of Cardiology*, Sep. 1974, vol. 34, pp. 325-332.

Primary Examiner—Francis Jaworski
Assistant Examiner—George Manuel
Attorney, Agent, or Firm—Fleit, Jacobson, Cohn, Price, Holman & Stern

[57] ABSTRACT

An implantable cardiac defibrillation/cardioversion electrode. The electrode is elongated and comprises a distal active region and a proximal lead region. Conductive discharge and insulative materials occupy distinct surfaces along the length of the active region. The active region is preformed to adopt a planar spiral patch configuration under relaxed conditions. Additional flexible preformed insulative and conductive discharge wings are provided to attach to the corresponding surfaces of the active region. A method of implantation of the spiral patch is disclosed for deployment by straightening the electrode and introducing the same through an opening that approximates the cross section of the straightened electrode.

17 Claims, 5 Drawing Sheets

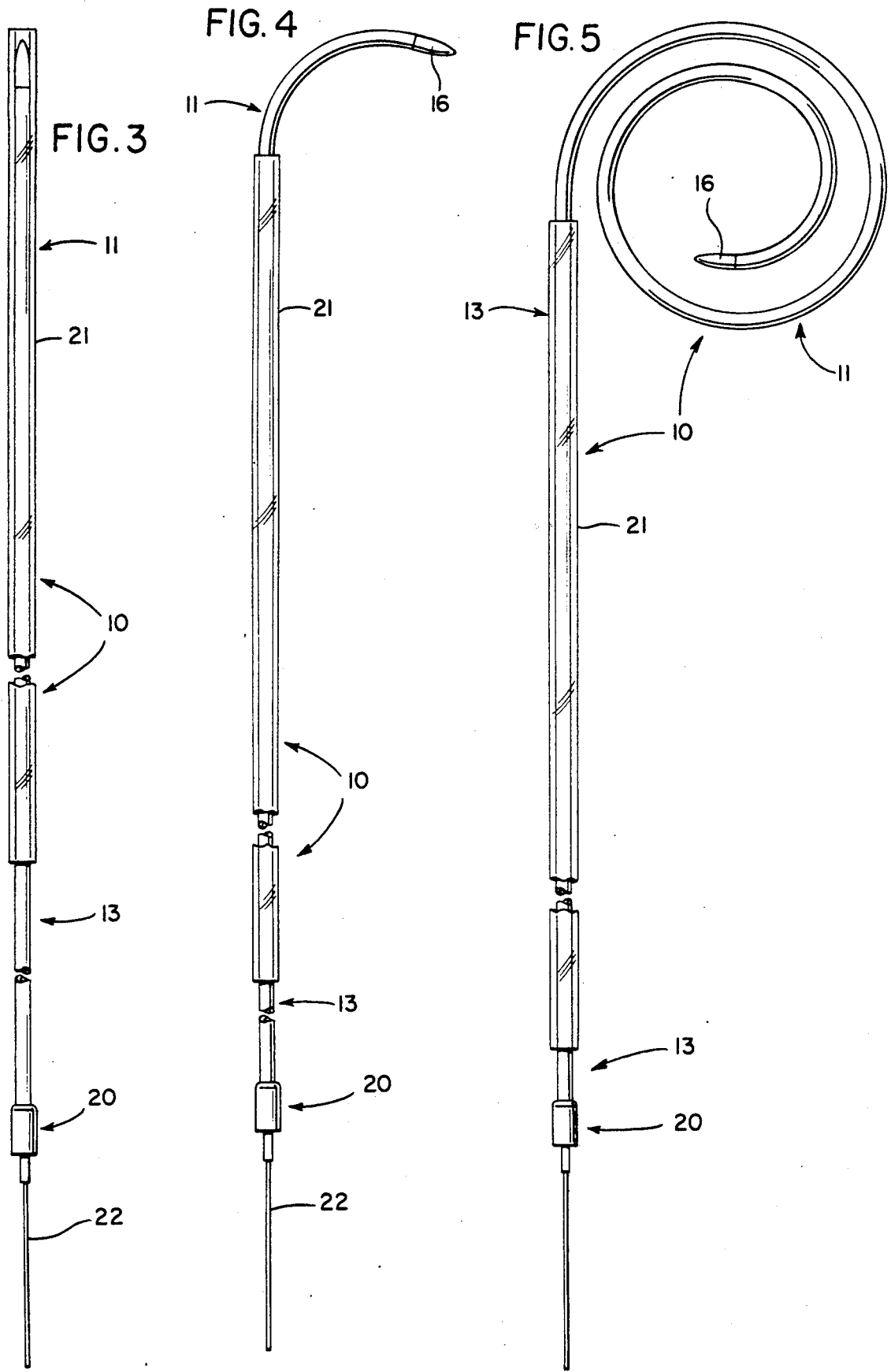

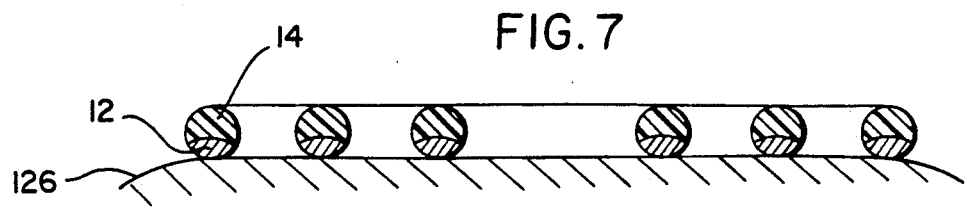
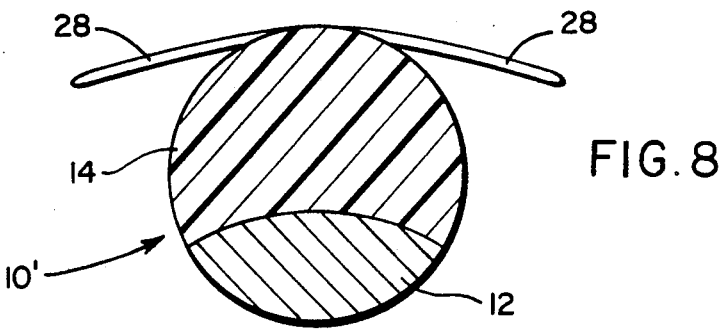
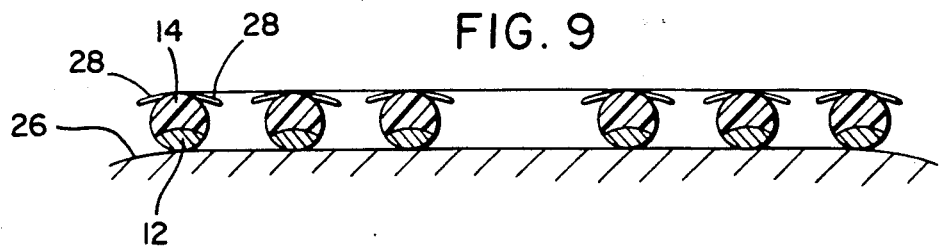
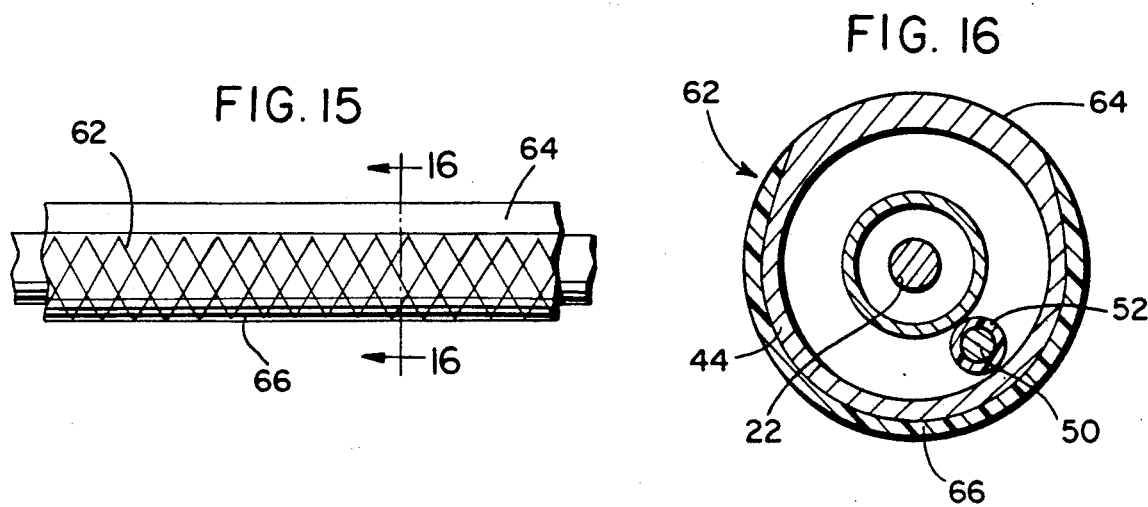
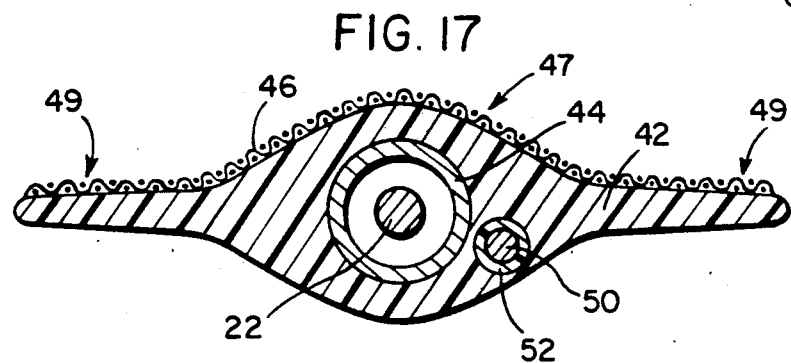

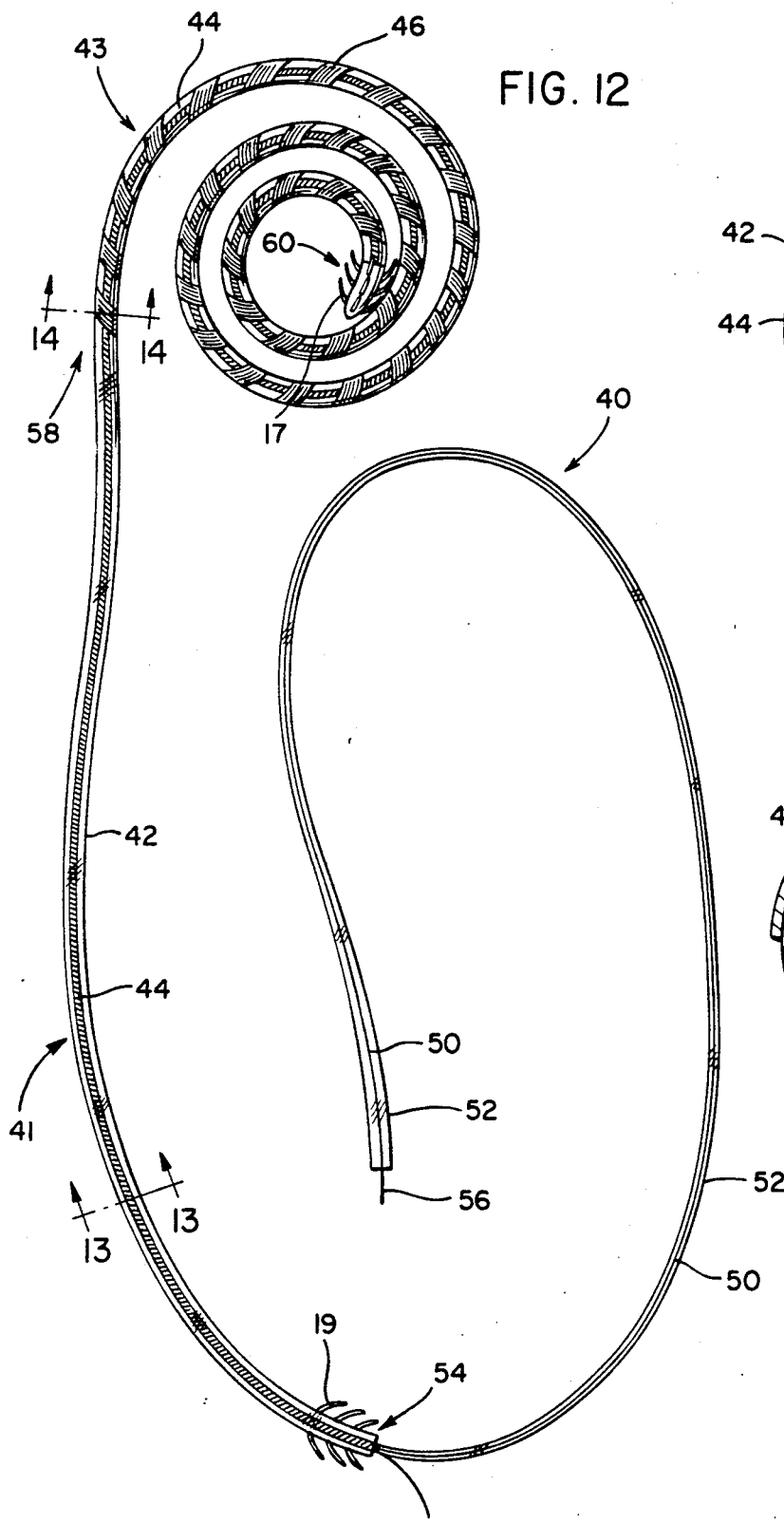
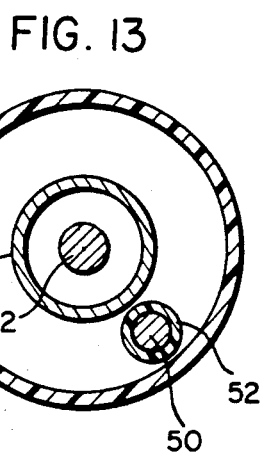
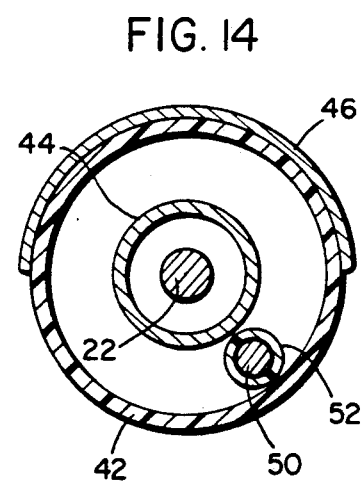

CARDIAC DEFIBRILLATION/CARDIOVERSION SPIRAL PATCH ELECTRODE

BACKGROUND OF THE INVENTION

The present application is a continuation-in-part of U.S. patent application Ser. No. 07/181,432, filed Apr. 14, 1988, entitled Cardiac Defibrillation/Cardioversion Spiral Patch Electrode, and now abandoned.

This invention relates to implantable electrical devices used to terminate or control ventricular or atrial tachyarrhythmias. More specifically, this invention is directed to an implantable defibrillation or cardioversion electrode and a method for placing the electrode on or about the heart to deliver electrical energy to the heart.

It is well known that one technique for arresting ventricular fibrillation is to place two electrodes on the surface of the heart to set up an electrical field between the electrodes when they are pulsed; this electric field eliminates the sporadic electrical charges present on the heart during ventricular fibrillation. The amount of surface area contacted by the electrodes is a major factor in determining how consistently and effectively the developed electric field will affect the fibrillating heart.

Presently, many defibrillation electrodes require major surgical procedures for insertion due to the complex structure of the electrode and the need for precise placement of the electrodes on the heart. These surgical procedures are not only costly to the patient, but raise risks associated with major surgery. There have been attempts to provide simplified placement procedures and lead configurations.

In the pacing field, where the discharge tips are small and the discharge energies are small, electrode design and placement has become quite advanced. For example, U.S. Pat. No. 3,865,118 to Bures and U.S. Pat. No. 3,289,138 to Halvoresen disclose pacing electrodes wherein insulated elongated conductor leads are inserted through an already positioned catheter. Both patents disclose insulated conductors having conductive electrode tips at the ends which spring outwardly to contact the atrial or ventricular walls when the catheter sheath surrounding the leads is removed from the body. The leads themselves are straightened for insertion into the catheter and are preformed to spring in a curved relation to facilitate contact with the heart walls.

In contrast to pacing electrodes, defibrillation/cardioversion electrodes deliver high discharge energies to the heart tissue (on the order of 20–35 joules, whereas pacing involves only microjoules); and whereas pacing electrodes stimulate the heart at small, localized areas, defibrillation/cardioversion electrodes discharge electrical energy through a major portion (critical mass) of the myocardium. It is for this reason that the defibrillation/cardioversion electrode of today has evolved into the patch electrode with a surface area somewhere in the range of 10 to 30 sq. cm.

The design and deployment of defibrillation/cardioversion electrodes also has evolved and has become more simplified. For example, in U.S. Pat. No. 4,567,900 to Moore, a defibrillator electrode is disclosed comprising a spring wire loop preformed to maintain an oval or circular configuration. Conductive foil extends transversely across the loop and is conductively secured to the loop to form a planar electrode surface. Prior to insertion into a delivery catheter, the wire loop assembly is collapsed to an elongated nonplanar configuration. Once the catheter containing the wire loop electrode is placed into position on the heart within the pericardial space, the catheter is withdrawn and the electrode expands into its planar configuration on the heart. In an alternative form disclosed by Moore, the wire loop is in a flattened coil configuration without the foilized strips.

While the Moore patent teaches the concept of a collapsible wire loop electrode, the method of collapsing and placing the electrode about the heart leaves room for improvement.

SUMMARY OF THE INVENTION

The present invention relates to an implantable defibrillation/cardioversion electrode and more specifically to a preformed spiral electrode lead and a simplified and relatively non-invasive method for its implantation.

It is a primary object of this invention to provide an effective defibrillation/cardioversion electrode which can be implanted in the body without major surgery.

It is another object of this invention to provide a cardiac defibrillation/cardioversion electrode having a simple structure but still providing effective electrode surface area for stimulating and sensing.

It is yet another object of this invention to provide a cardiac defibrillation/cardioversion electrode having a fixation means to facilitate implantation on or about the heart.

The inventive electrode comprises an elongated body having distinct conductive and insulative surface portions along the length of the electrode. The conductive and insulative surface portions of the electrode are preformed such that the electrode assumes a spiral patch configuration when relaxed. The conductive electrode surface portion may comprise a plurality of distinct surfaces to form a multiple electrode lead.

In addition, the electrode may be provided with preformed insulative or conductive discharge wings attached along its active region. The insulative wings are designed such that when the active region is in its relaxed coiled position, they spread out from the surface of the electrode to further focus the electrical discharge. The similarly designed conductive discharge wings provide additional discharge surface area and a degree of fixation of the electrode via tissue ingrowth after implantation.

Importantly, the electrode of the present invention, in one embodiment, has a generally circular cross section in its straightened configuration. Even with the insulative and/or conductive wings, the cross section of the electrode is small. Therefore, although the electrode takes a relatively large size after deployment, it can be deployed through a smaller space than any defibrillation/cardioversion electrode heretofore known.

The electrode of the present invention is straightened and implanted on the heart or in the pericardial space through a small incision or puncture in the pericardial sac, or is implanted percutaneously outside the pericardial space. Once in position, the straightened electrode assumes a relaxed spiral configuration such that the conductive surface portion faces towards the heart directing current to the heart surface. The fixation means may be in the form of anchor elements which project out from the electrode body, a screw-in tip, or a suture sleeve. Once in position proximate the heart, the fixation means is employed to stabilize the electrode relative to the heart.

The manner in which these and other objects are accomplished will become more readily apparent when reference is made to the following description, taken in conjunction with the accompanying drawings.

BRIEF DESCRIPTION OF THE DRAWINGS

FIGS. 3, 4 and 5 are views during various stages of implantation of the electrode illustrated in FIG. 1.

FIG. 7 is a cross section through line 7—7 of FIG. 6.

FIG. 8 is a cross section similar to FIG. 2 of a first alternative embodiment of the inventive electrode.

FIG. 9 is a cross section similar to FIG. 7 of the electrode illustrated in FIG. 8 when placed in association with the heart.

FIG. 12 is a perspective view of a cardiac defibrillation/cardioversion electrode in accordance with a third embodiment of the present invention.

FIG. 13 is a cross section through line 13—13 of FIG. 12.

FIG. 14 is a cross section through line 14—14 of FIG. 12.

FIG. 15 is a view of a conductive screen which attaches to the electrode similar to that illustrated in FIG. 12.

FIG. 16 is a cross section through line 16—16 of FIG. 15.

FIG. 17 is a cross section similar to that seen through line 14—14 of FIG. 12, but illustrating still a further alternative embodiment of the present invention.

DETAILED DESCRIPTION OF THE DRAWINGS

Figure 1:
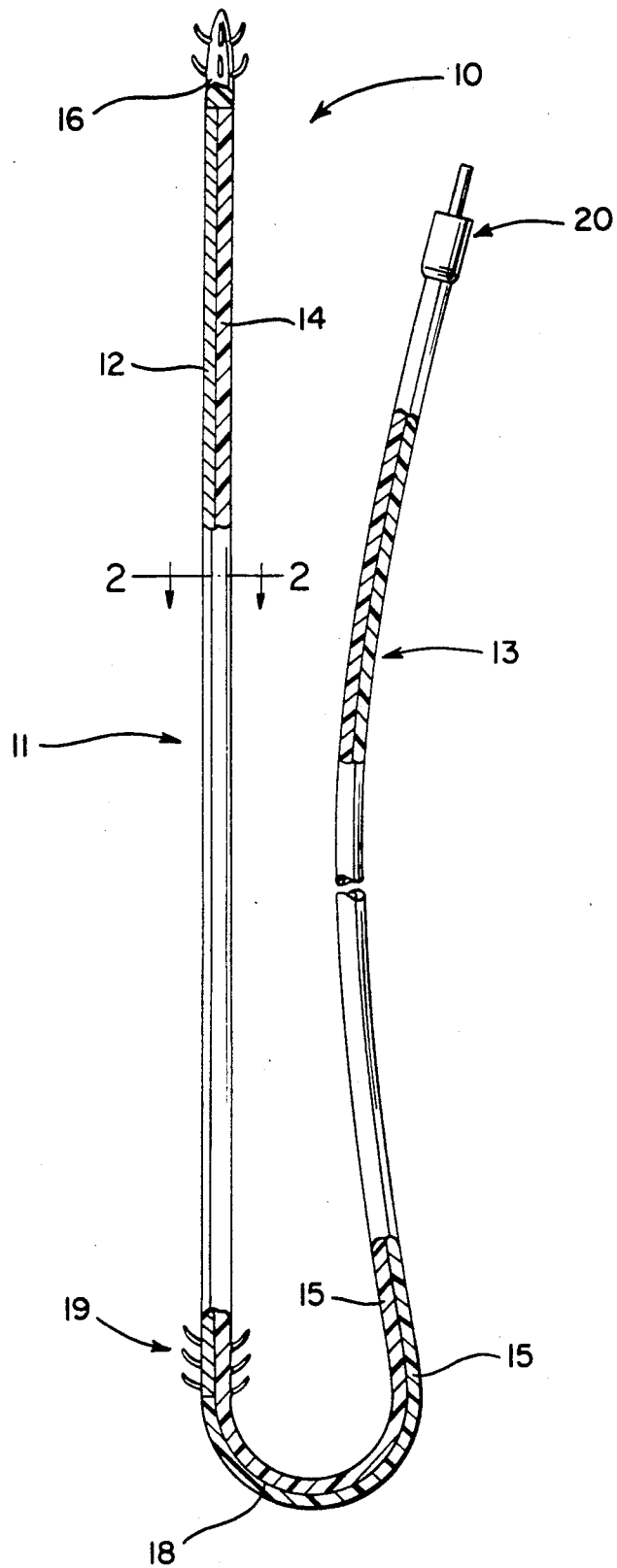
FIG. 1 is a perspective view of the inventive electrode in a partially straightened position.
Figure 2:
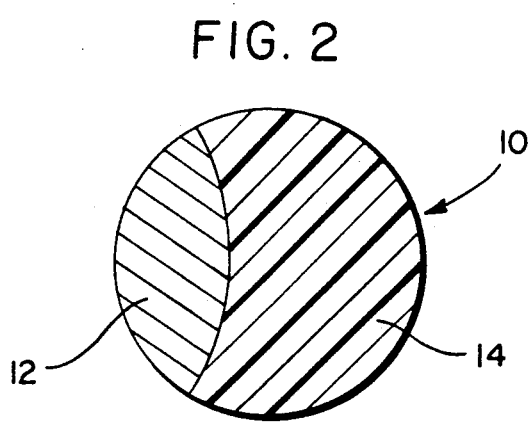
FIG. 2 is a cross section through line 2—2 of FIG. 1.

Referring first to FIGS. 1 and 2, the inventive spiral patch electrode is shown generally at 10 in a partially straightened condition. (The term electrode, as used hereinafter, includes both lead and conductive elements). The electrode 10 is thin and elongated and comprises a distal active region 11 and a proximal lead region 13. A conductive discharge surface 12 and an insulative surface 14 define and extend the entire length of the active region 11, and a tapered, soft, insulative tip 16 terminates the distal end of the active region. A conductive element 18 surrounded by an insulator 15 extends the entire length of the proximal lead region 13. The conductive element 18 is, for example, a lead of DBS wire, which electrically connects at one end with the conductive discharge surface 12. The opposite end of conductor 18 is connected to a terminal pin assembly 20 attached to the proximal end of the lead region 13. The conductive discharge surface 12 and the insulative surface 14 of the active region 11 are preformed so that the active region of the electrode 10 adopts a planar spiral patch shape (FIG. 6) when in its relaxed state.

The distal insulative tip 16 includes a fixation means 17 thereon to anchor and stabilize the electrode 10 relative to the heart. As illustrated, the fixation means 17 takes the form of anchor elements which anchor the tip 16 of the electrode 10 within the pericardial space. In addition, a proximal fixation means 19 is provided which is illustrated as being similar to fixation means 17 but anchors the electrode 10 at the location of entrance into the pericardial space as will be explained hereinafter.

Other fixation means are within the spirit and scope of this invention. For example, rather than the distal anchor elements 17 shown in FIG. 1, a screw-in tip can be used. If the line of electrode introduction is perpendicular to the plane of the deployed electrode, then the electrode will rotate as it is deployed. This rotation can be harnessed to provide the rotation necessary to screw the distal tip of the electrode into the myocardium or into the wall of the pericardial sac. Similarly, the fixation anchors 19 can be replaced by other anchoring means, such as the known suture sleeve, so that the surgeon can suture the proximal end of the electrode to the pericardial sac. The proximal anchoring means also can be placed at locations other than as specifically illustrated, and the precise placement of the anchor even can be determined by the surgeon during implantation.

In use, the electrode 10 preferably is placed in position in the pericardial space on the heart surface via a conformal catheter that is inserted through a small incision or puncture in the membrane defining the pericardial space surrounding the heart. The implantation procedure can best be understood by referring to FIGS. 3-5. A catheter 21, having a cross section only slightly larger than the cross section of the electrode 10, first is introduced through the skin and into the pericardial space; the electrode 10 then is inserted into the catheter 21, as by introducing a stylet 22 (or smooth plastic coated guidewire) through terminal pin 20 and a lumen in the body of electrode 10, thereby straightening the active region 11, as shown in FIG. 3. With the catheter 21 containing the electrode 10 and in position in the pericardial space surrounding the heart, the active region 11 of electrode 10 is urged out of the catheter with the aid of the stylet 22. The active region 11 then emerges from catheter 21, with the stylet 22 being withdrawn as appropriate, and begins to take its relaxed, coiled shape in the pericardial space, as shown in FIG. 4. As the active region 11 continues to emerge from the catheter 21, it assumes more of its relaxed planar spiral shape, as shown in FIG. 5. Deployment then is continued until the entire active portion 11 of the electrode 10 is in place in the pericardial space. The stylet 22 and the catheter 21 are then removed, and the proximal lead region 13 of electrode 10 is tunneled to the location where it will be connected to the pulse generator of the defibrillation/cardioversion system.

For ease of illustration, the line of electrode introduction defined by catheter 21 is shown in the plane of the deployed active region 11 of electrode 10. However, as explained above, this need not be the case. Rather, for example, the line of electrode introduction can be perpendicular to the desired plane of the active region 11 after deployment.

Figure 6:
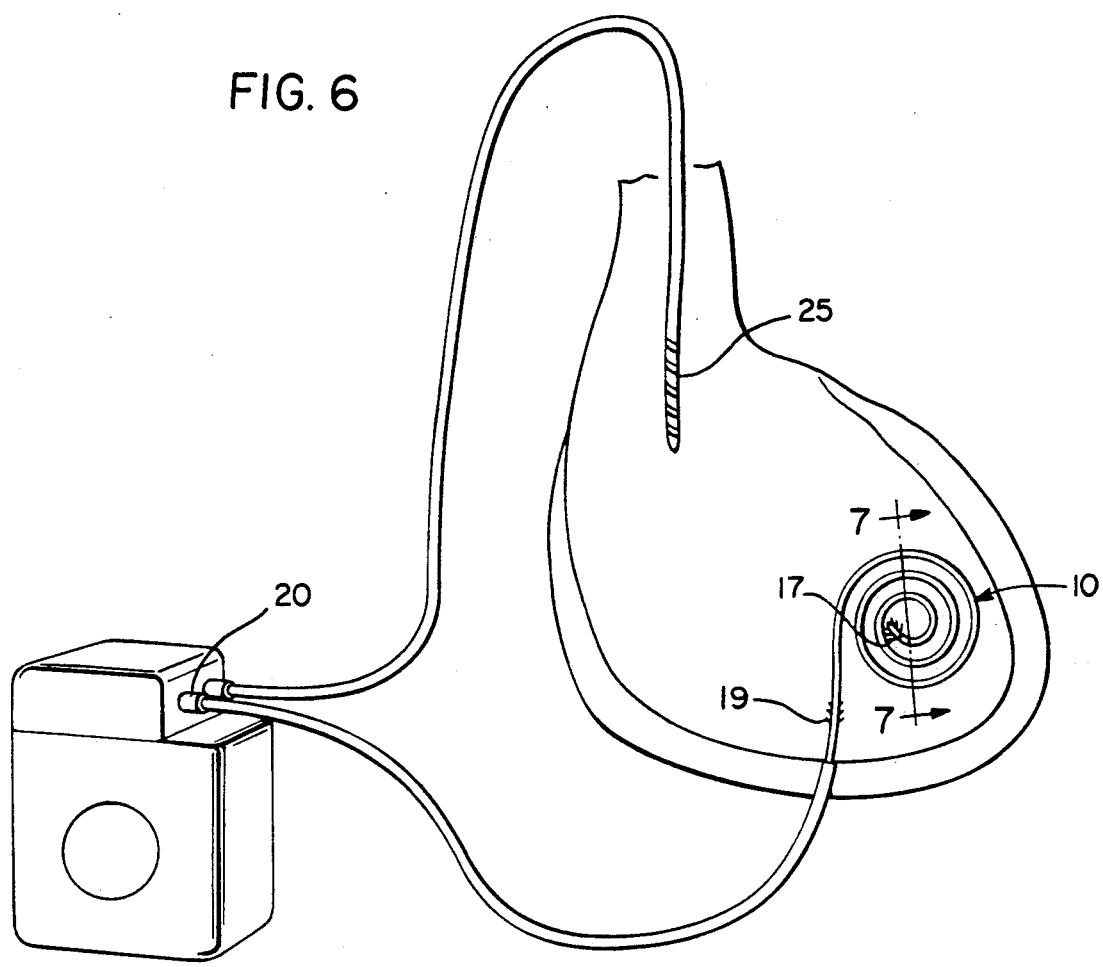
FIG. 6 is a diagram of the inventive electrode placed in association with the heart in a complete defibrillation/cardioversion system.

FIG. 6 shows the electrode 10 in its relaxed spiral patch form implanted on the heart as part of a defibrillation system. The fixation means 19 stabilizes the electrode 10 at the location of entrance into the pericardial space while the distal fixation means 17 anchors the electrode in the center of the deployed spiral patch portion of electrode 10. The electrode 10 is connected to a pulse generator 23 via terminal pin assembly 20. A second electrode 25 also is plugged into the pulse generator 23. Electrode 25 could be a spiral patch electrode 10 of the present invention, a superior vena cava catheter electrode (as illustrated), or another type of electrode known in the art.

Although not illustrated, it is contemplated that the complete defibrillation/cardioversion system include a set of ECG sensing electrodes located in the right ventricle or screwed directly into the myocardium. Also, as is well known in the art, the electrode pair 10, 25 could be used for morphology sensing, along with the ECG electrodes, and a pacing tip could be provided.

With reference to FIG. 7, the specific orientation of the implanted spiral patch electrode 10 on the heart surface 26 can be seen. As is well known, implantable defibrillation/ cardioversion through implanted surface electrodes requires the focused discharge of electrical energy into the heart. This is accomplished in the present invention by the discharge electrode having a conformal conductive surface facing the heart and a conformal insulative surface facing away from the heart. Therefore, the electrode of the present invention is designed so that after deployment and when in its relaxed spiral configuration, the conductive discharge surface 12 is oriented facing the heart so that current is directed towards the heart surface 26. Current is prevented from passing away from the heart by the orientation of insulative surface 14 facing away from the heart. As can be seen in FIGS. 6 and 7, the spiral patch electrode 10, in its relaxed state, is defined by spaced coils so that the electrode provides a large discharge surface area for stimulation and sensing.

The tightness of the spiral windings, the overall surface area of the electrode, and the effective discharge surface area of the spiraled electrode can be varied to satisfy specific heart sizes and discharge requirements; but these can be determined from considerations known to the art. It is contemplated, however, that the spiraled electrode present an effective discharge area in the range of 10 to 30 sq. cm., similar to that of the known patch electrode.

FIG. 8 illustrates a first alternative embodiment of the inventive electrode, shown at 10'. Specifically, the electrode 10' is provided with preformed insulative wings 28 attached to (or formed with) the insulative surface 14 along substantially the entire active region 11 of the electrode 10' As shown in FIG. 9, the insulative wings 28 are preformed to deploy when the electrode 10' is in its relaxes spiral patch configuration, and to spread out from the surface of the electrode 10' to further focus the electrical discharge towards the heart surface 26.

Figure 10:
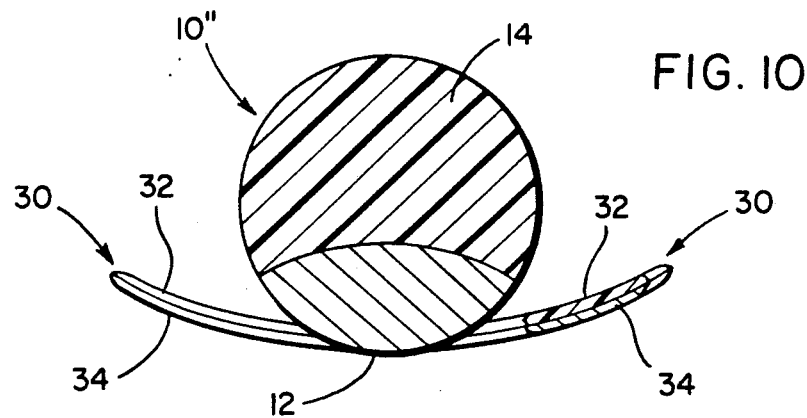
FIG. 10 is a cross section similar to FIG. 2 of a second alternative embodiment of the inventive electrode.

FIG. 10 illustrates a second alternative embodiment of the electrode, shown at 10''. Specifically, the electrode 10'' is provided with preformed discharge wings 30 having conductive discharge surfaces 34 and insulative surfaces 32. The wings 30 are attached to the conductive discharge surface 12 substantially along the entire active region 11 of the lead 10.

Figure 11:
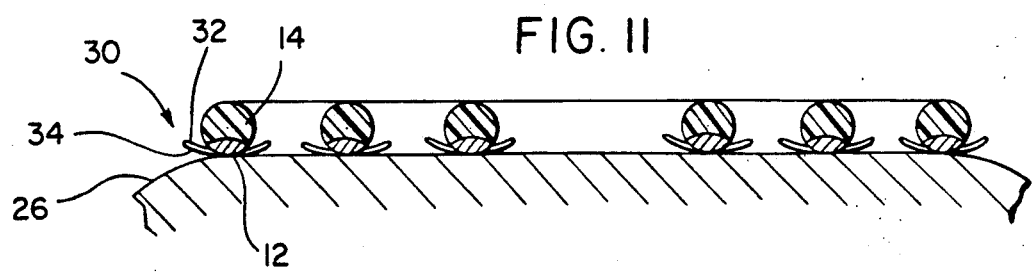
FIG. 11 is a cross section similar to FIG. 7 of the electrode illustrated in FIG. 10 when placed in association with the heart.

Referring to FIG. 11, the discharge wings 30 spread toward the heart surface 26 when the electrode 10 is in its relaxed spiral orientation in the pericardial space, placing the conductive discharge surfaces 34 in close contact with the heart surface 26 to provide additional discharge surface area. Furthermore, wings 30, if desired, could be designed to provide a degree of fixation via tissue ingrowth after implantation.

It should be noted that the insulative wings 28 shown in FIG. 8 and the discharge wings 30 shown in FIG. 10 are designed to conform to the cross section of the electrode main body so that when being deployed, the guiding catheter can still be only slightly larger in cross section than the electrode itself. Also, it is possible to combine on a single electrode, insulative wings 28 and discharge wings 30.

FIGS. 12-14 illustrate the spiral patch defibrillation electrode 40 in accordance with a third embodiment of the present invention. The electrode 40 is similar to electrode 10 of FIG. 1, and is straightened with the stylet 22 as will be explained in more detail hereinafter.

Electrode 40 comprises a silicone rubber tubular body 42 enclosing a multifilar coil 44. The tubular body 42 comprises a proximal lead region 41 and a distal active region 43. The tubular body 42 is preformed into a spiral shape and supports a conductive screen 46 along the active region 43 thereof. A low resistance DBS cable 50 enclosed by a silicone insulator tubing 52 extends through the proximal end 54 of the proximal lead region 41 of the tubing body 42 and runs from a terminal pin 56 at the proximal end of the electrode 40, to the conductive screen 46. The cable 50 connects to both the proximal end 58 and the distal end 60 of the conductive screen 46. As an alternative, tubular body 42 could be a multi-lumen tube so that one lumen could house the DBS cable 50 and another could serve to receive the stylet/coil or the guidewire.

The coil 44 is preferably formed of nitinol wire, and is also preformed into a spiral shape. Nitinol is a nickel-titanium alloy which has thermal "memory". Therefore, when the preformed spiral is straightened for implantation and then introduced into the body, the body heat warms the electrode so that the distal end of the electrode returns to its "memorized" spiral shape.

The conductive screen 46 is preferably formed of a fine mesh of platinum-iridium. The screen is folded upon itself to make two layers and is then wrapped around the active region 43 of the body 42 in a "barber pole" stripe style as illustrated in FIG. 12.

As shown in FIG. 12, the electrode 40 adopts a spiral configuration in its relaxed state similar to electrode 10 illustrated in FIG. 5. The coil 44 acts as a guide for the stylet 22. The stylet 22 is insertable, at the proximal end 54 of the body 42, into the coil 44. Because the stylet is a straight elongated element, the electrode 40 will straighten as the stylet is introduced into the coil 44. Specifically, both the preformed coil 44 and preformed body 42 are straightened as the stylet passes therethrough.

In use, the stylet 22 is inserted into the coil 44 to the distal end 60 of the conductive screen 46 along the length of the electrode 40. Thereafter, the electrode is guided to the pericardial space as shown in FIG. 6 where the stylet 22 is carefully removed so that the distal active region 43 of the body 42 will adopt a spiral configuration in the pericardial space. To concentrate the discharge energy from the conductive screen 46 to the heart, the surface of the body 42 at the distal active region 43, not facing the heart, is insulated. This insulation may be similar to that of electrode 10 of FIG. 1.

When in its relaxed planar spiral configuration, the electrode 40 deploys a plurality of spaced conductive surfaces along the active region thereof. As such, a plurality of conductive edges are created which contribute to a uniform distribution of energy to the heart.

Referring to FIG. 17, the silicone rubber tubing body 42 of electrode 40 may be molded into a substantially flat sheet. This sheet would also be preformed to adopt a planar spiral configuration and would support a conductive screen 46. In this arrangement, more conductive screen would be in direct contact with the heart because screen 46 occupies both the round surface region 47 and the flat surface regions 49. To straighten, the electrode 40 is inserted into a catheter (or is combined with a stylet or guidewire), similar to the manner in which electrode 10 in FIGS. 3-5 is straightened for implantation. Alternatively, the flat profile can be achieved by heating a polyurethane body and pressing it to form the flat shape. Further, the sheet is preformed so that at deployment the surface of the sheet supporting the conductive screen faces the heart surface. It is contemplated that the deployed active region of the flat electrode be such that the plane of the deployed spiral also be the plane of the flat surface of the electrode.

Further, the silicone rubber tubing body 42 could be replaced by a polyurethane tubing body preformed into a spiral shape. Also, the conductive screen 46 could be replaced by a continuous conductive wire braided sock 62, illustrated in FIGS. 15 and 16. The electrode utilizing the sock 62 has an exposed surface 64 and an insulated surface 66 to focus the discharge. The wire braided sock 62 provides a continuous conductive surface on the active region 43, and could be similar to the wire braid that reinforces the tubing wall of some angiographic catheters.

To create the insulative surface 66 and the conductive surface 64, the body 42 may be extruded by an off-center extrusion process so that the conductive screen 46 is exposed on one face of the body 42, but encapsulated into the tubing body 42 on the opposite face. This is only one way to achieve the discrete insulative and conductive surfaces. Another way is to coat only the surface of the body 42 not facing the heart with an insulative material, as by masking the electrode surface where it is desired, that the conductive material be exposed, extruding a layer of insulation, and then removing the mask to expose the electrode surface.

The defibrillation/cardioversion electrode of the present invention may be provided with additional separate conductive surfaces to perform ECG sensing, cardiac pacing, and other cardioversion, sensing, and stimulating functions. Furthermore, while the inventive electrode has been described primarily for use in the pericardial space, it is contemplated that the electrode can be used wherever a large surface area patch electrode is needed. Additionally, it is contemplated that implantation of the inventive electrode can be accomplished both percutaneously outside the pericardial space and in the pericardial space by manipulation of a stylet rather than by use of a guiding catheter. Also, while not illustrated, a separate flexible, shape-retaining member may form a part of the electrode active region to enable the electrode to adopt its relaxed planar spiral shape. Other variations also are envisaged within the scope of the present invention, just as long as the principle of deploying a large surface area spiral electrode through an opening having a cross section substantially the same as that of an individual winding of the spiral itself is retained.

It should be understood, therefore, that the above description is intended as an example only, and is not intended to limit the present invention except as set forth in the following claims.

We claim:
1. A cardiac defibrillation/cardioversion electrode lead device for implantation in the region of the human heart for connection to a defibrillation/cardioversion unit, said device comprising:
   an elongated tubular body having a distal active region and a proximal lead region, said elongated tubular body being preformed to adopt a planar spiral configuration in its relaxed state;
   a coil coextensive with and contained within said tubular body;
   a conductive discharge surface extending along substantially the entire length of said active region of said tubular body, and occupying only a portion of the surface of said active region, said conductive discharge surface comprising at least one layer of conductive screen wrapped around the length of said active region of said tubular body;
   an insulative surface coextensive with said active region on the remainder of the surface of said active region;
   an insulated conductor means extending within said elongated tubular body having proximal and distal ends, said distal end being connected to said conductive discharge surface;
   connector means attached to the proximal end of said insulated conductor means for electrically connecting said insulated conductor means to said defibrillation/cardioversion unit; and
   an elongated straightening means movable relative to said coil substantially along the entire length thereof for straightening said elongated tubular body for implanting said device proximate the heart, and so that when said straightening means is withdrawn from said coil, said tubular body adopts a planar spiral configuration with said conductive surface on one face thereof and said insulative surface on the opposite face thereof.

2. The electrode lead device of claim 1, wherein said conductive screen is wrapped so that space is provided between adjacent turns thereof.

3. The electrode lead device of claim 1, wherein said conductive screen is formed of platinum-iridium mesh.

4. The electrode lead device of claim 1, wherein said elongated tubular body is molded into a substantially flat cross section and defining a rounded surface region and flat surface regions on the active region thereof, said conductive screen being supported on said rounded surface region and said flat surface regions.

5. A cardiac defibrillation/cardioversion electrode lead device for implantation in the region of the human heart for connection to a defibrillation/cardioversion unit, said device comprising:
   an elongated tubular body having a distal active region and a proximal lead region, said elongated tubular body being preformed to adopt a planar spiral configuration in its relaxed state;
   a coil coextensive with and contained within said tubular body;
   a conductive discharge surface extending along substantially the entire length of said active region of said tubular body, and occupying only a portion of the surface of said active region, said conductive discharge surface comprising conductive wires braided to form a conductive sock which occupies the active region of the tubular body;

an insulative surface coextensive with said active region on the remainder of the surface of said active region;

an insulated conductor means extending within said elongated tubular body having proximal and distal ends, said distal end being connected to said conductive discharge surface;

connector means attached to the proximal end of said insulated conductor means for electrically connecting said insulated conductor means to said defibrillation/cardioversion unit; and an elongated straightening means movable relative to said coil substantially along the entire length thereof for straightening said elongated tubular body for implanting said device proximate the heart, and so that when said straightening means is withdrawn from said coil, said tubular body adopts a planar spiral configuration with said conductive surface on one face thereof and said insulative surface on the opposite face thereof.

6. The electrode lead device of claim 5, wherein said tubular body is made of an insulative material and is formed by an extrusion process so that said conductive wires are on the surface of one portion of said active region and are buried in said insulative material on said remainder of the surface of said tubular body.

7. A cardiac defibrillation/cardioversion electrode lead device for implantation in the region of the human heart for connection to a defibrillation/cardioversion unit, said device comprising:

an elongated tubular body having a distal active region and a proximal lead region, said elongated tubular body being preformed to adopt a planar spiral configuration in its relaxed state;

a coil coextensive with and contained within said tubular body;

a conductive discharge surface extending along substantially the entire length of said active region of said tubular body, and occupying only a portion of the surface of said active region;

an insulative surface coextensive with said active region on the remainder of the surface of said active region;

an insulated conductor means extending within said elongated tubular body having proximal and distal ends, said distal end being connected to said conductive discharge surface;

connector means attached to the proximal end of said insulated conductor means for electrically connecting said insulated conductor means to said defibrillation/cardioversion unit;

fixation means on the active region of said tubular body for anchoring said device relative to the heart; and an elongated straightening means movable relative to said coil substantially along the entire length thereof for straightening said elongated tubular body for implanting said device proximate the heart, and so that when said straightening means is withdrawn from said coil, said tubular body adopts a planar spiral configuration with said conductive surface on one face thereof and said insulative surface on the opposite face thereof.

8. A cardiac defibrillation/cardioversion electrode lead device for implantation in the region of the human heart for connection to a defibrillation/cardioversion unit, said device comprising:

an elongated tubular body having a distal active region and a proximal lead region, said elongated tubular body being preformed to adopt a planar spiral configuration in its relaxed state;

a coil coextensive with and contained within said tubular body, said coil being formed of nitinol wire;

a conductive discharge surface extending along substantially the entire length of said active region of said tubular body, and occupying only a portion of the surface of said active region;

an insulative surface coextensive with said active region on the remainder of the surface of said active region;

an insulated conductor means extending within said elongated tubular body having proximal and distal ends, said distal end being connected to said conductive discharge surface;

connector means attached to the proximal end of said insulated conductor means for electrically connecting said insulated conductor means to said defibrillation/cardioversion unit; and an elongated straightening means movable relative to said coil substantially along the entire length thereof for straightening said elongated tubular body for implanting said device proximate the heart, and so that when said straightening means is withdrawn from said coil, said tubular body adopts a planar spiral configuration with said conductive surface on one face thereof and said insulative surface on the opposite face thereof.

9. A cardiac defibrillation/cardioversion electrode lead device for implantation in the region of the human heart for connection to a defibrillation/cardioversion unit, said device comprising:

a conductive discharge surface extending along substantially the entire length of said active region of said tubular body, and occupying only a portion of the surface of said active region;

an elongated tubular body having a distal active region and a proximal lead region, said elongated tubular body being preformed to adopt a planar spiral configuration in its relaxed state, said tubular body being made of insulative material and being formed by an extrusion process so that said conductive discharge surface and said insulative surface occupy distinct surfaces along the active region of said tubular body;

a coil coextensive with and contained within said tubular body;

an insulative surface coextensive with said active region on the remainder of the surface of said active region;

an insulated conductor means extending within said elongated tubular body having proximal and distal ends, said distal end being connected to said conductive discharge surface; connector means attached to the proximal end of said insulated conductor means for electrically connecting said insulated conductor means to said defibrillation/cardioversion unit; and an elongated straightening means movable relative to said coil substantially along the entire length thereof for straightening said elongated tubular body for implanting said device proximate the heart, and so that when said straightening means is withdrawn from said coil, said tubular body adopts a planar spiral configuration with said conductive surface on one face thereof and said insulative surface on the opposite face thereof.

10. A cardiac defibrillation/cardioversion electrode lead device for implantation in the region of the human heart for connection to a defibrillation/cardioversion unit, the device comprising:
- an elongated, thin body having a distal active region and a proximal lead region and a substantially uniform cross section throughout its length;
- a conductive discharge surface extending along substantially the entire length of said active region, and occupying only a portion of the surface of said active region, said conductive discharge surface comprising a conductive screen spiralled around the elongated tubular body;
- an insulative surface coextensive with said conductive discharge surface and occupying substantially the remainder of the surface of said active region;
- conductor means extending along substantially the entire length of said lead region and electrically connecting at least one location thereof to said conductive discharge surface;
- insulator means surrounding said conductor means;
- connector means on the end of said proximal lead region remote from said active region for electrically connecting said conductor means to said defibrillation/cardioversion unit;
- straightening means for introducing said electrode to the region of the human heart; and
- said distal active region being flexible and being preformed so that it can be substantially straightened by said straightening means for insertion and so that when said straightening means is removed, it adopts a substantially planar spiral configuration with said conductive discharge surface on one face thereof and with said insulative surface on the opposite face thereof.

11. The electrode lead device of claim 10, wherein said conductive screen is formed of platinum-iridium mesh.

12. The electrode lead device of claim 10, wherein said elongated body is pressed into a substantially flat cross section and defining a rounded surface region and flat surface regions on the active region thereof, said conductive screen being supported on said rounded surface region and said flat surface regions.

13. A cardiac defibrillation/cardioversion electrode lead device for implantation in the region of the human heart for connection to a defibrillation/cardioversion unit, the device comprising:
- an elongated, thin body having a distal active region and a proximal lead region and a substantially uniform cross section throughout its length;
- a conductive discharge surface extending along substantially the entire length of said active region, and occupying only a portion of the surface of said active region, said conductive discharge surface comprising conductive wires braided to form a conductive sock which occupies the active region of the elongated body;
- an insulative surface coextensive with said conductive discharge surface and occupying substantially the remainder of the surface of said active region;
- conductor means extending along substantially the entire length of said lead region and electrically connecting at least one location thereof to said conductive discharge surface;
- insulator means surrounding said conductor means;
- connector means on the end of said proximal lead region remote from said active region for electrically connecting said conductor means to said defibrillation/cardioversion unit;
- straightening means for introducing said electrode to the region of the human heart; and
- said distal active region being flexible and being preformed so that it can be substantially straightened by said straightening means for insertion and so that when said straightening means is removed, it adopts a substantially planar spiral configuration with said conductive discharge surface on one face thereof and with said insulative surface on the opposite face thereof.

14. A cardiac defibrillation/cardioversion electrode lead device for implantation in the region of the human heart for connection to a defibrillation/cardioversion unit, the device comprising:
- an elongated, thin body having a distal active region and a proximal lead region and a substantially uniform cross section throughout its length;
- a coil coextensive with and contained within said thin body, said coil formed of nitinol wire;
- a conductive discharge surface extending along substantially the entire length of said active region, and occupying only a portion of the surface of said active region;
- an insulative surface coextensive with said conductive discharge surface and occupying substantially the remainder of the surface of said active region;
- conductor means extending along substantially the entire length of said lead region and electrically connecting at least one location thereof to said conductive discharge surface;
- insulator means surrounding said conductor means;
- connector means on the end of said proximal lead region remote from said active region for electrically connecting said conductor means to said defibrillation/cardioversion unit;
- straightening means for introducing said electrode to the region of the human heart;
- said distal active region being flexible and being preformed so that it can be substantially straightened by said straightening means for insertion and so that when said straightening means is removed, it adopts a substantially planar spiral configuration with said conductive discharge surface on one face thereof and with said insulative surface on the opposite face thereof.

15. A cardiac defibrillation/cardioversion electrode lead device for implantation in the region of the human heart for connection to a defibrillation/cardioversion unit, the device comprising:
- an elongated, thin body having a distal active region and a proximal lead region and a substantially uniform cross section throughout its length;
- fixation means on the distal active region of said elongated body for stabilizing said device relative to the heart;
- a conductive discharge surface extending along substantially the entire length of said active region, and occupying only a portion of the surface of said active region;
- an insulative surface coextensive with said conductive discharge surface and occupying substantially the remainder of the surface of said active region;
- conductor means extending along substantially the entire length of said lead region and electrically connecting at least one location thereof to said conductive discharge surface;

insulator means surrounding said conductor means;

connector means on the end of said proximal lead region remote from said active region for electrically connecting said conductor means to said defibrillation/cardioversion unit;

straightening means for introducing said electrode to the region of the human heart; and said distal active region being flexible and being preformed so that it can be substantially straightened by said straightening means for insertion and so that when said straightening means is removed, it adopts a substantially planar spiral configuration with said conductive discharge surface on one face thereof and with said insulative surface on the opposite face thereof.

16. A cardiac defibrillation/cardioversion electrode lead device for implantation in the region of the human heart for connection to a defibrillation/cardioversion unit, the device comprising:

an elongated, thin body having a distal active region and a proximal lead region and a substantially uniform cross section throughout its length;

a conductive discharge surface extending along substantially the entire length of said active region, and occupying only a portion of the surface of said active region;

an insulative surface coextensive with said conductive discharge surface and occupying substantially the remainder of the surface of said active region;

narrow, flexible planar wings formed of insulative material, attached to and coextensive with said insulative surface, and adapted to extend outward in opposite directions from a common longitudinal line on said insulative surface, said planar wings being preformed so that they can be retracted flush against the surface of said active region, and so that when said electrode is in its relaxed state, the wings deploy to a spread configuration away from the surface of said active region;

conductor means extending along substantially the entire length of said lead region and electrically connecting at least one location thereof to said conductive discharge surface;

insulator means surrounding said conductor means;

connector means on the end of said proximal lead region remote from said active region for electrically connecting said conductor means to said defibrillation/cardioversion unit;

straightening means for introducing said electrode to the region of the human heart; and said distal active region being flexible and being preformed so that it can be substantially straightened by said straightening means for insertion and so that when said straightening means is removed, it adopts a substantially planar spiral configuration with said conductive discharge surface on one face thereof and with said insulative surface on the opposite face thereof.

17. A cardiac defibrillation/cardioversion electrode lead device for implantation in the region of the human heart for connection to a defibrillation/cardioversion unit, the device comprising:

an elongated, thin body having a distal active region and a proximal lead region and a substantially uniform cross section throughout its length;

a conductive discharge surface extending along substantially the entire length of said active region, and occupying only a portion of the surface of said active region;

an insulative surface coextensive with said conductive discharge surface and occupying substantially the remainder of the surface of said active region;

narrow, flexible planar wings having a conductive face adjacent and connected to said conductive discharge surface and an insulative surface on the opposite side thereof, said wings being attached to and coextensive with said conductive discharge surface and adapted to extend outward in opposite directions from a common longitudinal line on said conductive discharge surface, said wings being preformed so that they can be retracted flush against said surface of the distal active region, and so that when said electrode is in its relaxed state, the wings deploy to a spread configuration away from the surface of said active region;

conductor means extending along substantially the entire length of said lead region and electrically connecting at least one location thereof to said conductive discharge surface;

insulator means surrounding said conductor means;

connector means on the end of said proximal lead region remote from said active region for electrically connecting said conductor means to said defibrillation/cardioversion unit;

straightening means for introducing said electrode to the region of the human heart; and said distal active region being flexible and being preformed so that it can be substantially straightened by said straightening means for insertion and so that when said straightening means is removed, it adopts a substantially planar spiral configuration with said conductive discharge surface on one face thereof and with said insulative surface on the opposite face thereof.

* * * * *